United States Patent [19]

Morris et al.

[11] Patent Number: 4,543,429

[45] Date of Patent: Sep. 24, 1985

[54] 1(7)-P-MENTHEN-9-AL

[75] Inventors: Anthony F. Morris, Gingins; Francois Delay, Carouge; Fritz Gautschi, Commugny; Alan F. Thomas, Borex; Wolfgang K. Giersch, Bernex; André Boschung, Gilly, all of, Switzerland

[73] Assignee: Firmenich SA, Geneva, Switzerland

[21] Appl. No.: 470,436

[22] Filed: Feb. 28, 1983

[51] Int. Cl.$^4$ .................. C07G 45/51; C07C 47/225
[52] U.S. Cl. .................. 568/446; 568/420; 568/443
[58] Field of Search .......... 568/446, 443, 450, 420

[56] References Cited

U.S. PATENT DOCUMENTS

| | | | |
|---|---|---|---|
| 2,710,825 | 6/1955 | Lazier et al. | 568/420 |
| 3,824,291 | 7/1974 | Pawson et al. | 260/340.9 |
| 3,917,652 | 11/1975 | Pawson et al. | 260/340.9 |

FOREIGN PATENT DOCUMENTS 0092031  10/1983  European Pat. Off. ............ 420/

OTHER PUBLICATIONS

Nomura et al., "Chemical Abstracts", vol. 90(25), 204267k, (19).
Albaiges et al., "Chemical Abstracts", vol. 74(15), 76537d, (1971), vol. 74, (1971), 100227a.

*Primary Examiner*—Werren B. Lone
*Attorney, Agent, or Firm*—Pennie & Edmonds

[57] ABSTRACT

1(7)-p-Methen-9-al, a novel terpene aldehyde, possesses useful organoleptic properties and develops bitter, herbal and aromatic perfume notes. In the field of flavors, 1(7)-p-menthen-9-al develops flowery, herbal and fatty characters reminiscent of certain aspects of the flavor of nuts or cumin.

2 Claims, No Drawings

1(7)-P-MENTHEN-9-AL

BRIEF SUMMARY OF THE INVENTION

This invention relates to the field of perfumery and flavors; more particularly, it provides a novel terpene aldehyde of formula

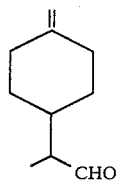
(I)

or 1(7)-p-menthen-9-al.

The instant invention also provides a perfuming or a flavoring composition which comprises 1(7)-p-menthen-9-al as active ingredient.

Further, this invention provides a method to impart, enhance or modify the fragrance properties of perfumes and perfumed products, or the gustative properties of foodstuffs and beverages in general, which method comprises the step of adding thereto an effective amount of 1(7)-p-menthen-9-al.

This invention also concerns a process for the preparation of 1(7)-p-menthen-9-al which process converts in four reaction steps 7,8-dihydroxy-p-menthane into the desired terpene aldehyde.

BACKGROUND OF THE INVENTION 1-p-Menthen-9-al, an isomer of compound (I), is known in the art of perfumery for its green and fatty note which is reminiscent of the odor of gingergrass. This compound possesses moreover a flowery, herbal, sweet and lactonic character of cumarin type. In contradistinction therefrom, 1(7)-p-menthen-9-al of the invention is characterized by a flowery, herbal and somewhat fatty scent reminiscent of certain aspects of the odor developed by nuts or cumin. For all practical applications, in view of their respective properties, it has become apparent that the compound of the invention cannot be replaced by the known isomer of the prior art.

PREFERRED EMBODIMENTS OF THE INVENTION

The proportion in which 1(7)-p-menthen-9-al is used in order to achieve the desired results can vary within a wide range. Owing to its olfactive power, concentrations of the order of 0.01 to 0.1-0.5% by weight, based on the total weight of the composition to which it is added, can already promote a marked effect.

In the field of flavors, these proportions can be of the order of a few parts per million. Typically, concentrations of about 1 to 10 ppm are sufficient to achieve the desired aromatization of foodstuffs and beverages in general, more particularly of decoctions, infusions and tobacco. 1(7)-p-Menthen-9-al is prepared according to the invention by a process which comprises the following sequential steps:

(a) treating 7,8-dihydroxy-p-menthane with an acetylating agent to give 7-acetoxy-8-hydroxy-p-menthane;
(b) dehydrating the obtained compound to yield 7-acetoxy-8-p-menthene;
(c) epoxydizing this latter compound to give 7-acetoxy-8,9-epoxy-p-menthane, and
(d) subjecting the said epoxyde to a thermal treatment to give a pyrolysate essentially consisting of the desired 1(7)-p-menthen-9-al.

The different steps of the above described process are carried out according to current techniques. Thus, step (a) is effected by means of an ordinary acetylating agent, for instance by acetic anhydride in the presence of pyridine.

Dehydration is carried out by means of alumina. According to a preferred mode of operation, the dehydration is effected by passing a solution of starting hydroxy-acetate in an inert organic solvent through a column filled with γ-alumina mixed with quartz sand, the column being prior heated to 250° C. The condensate which is obtained by cooling the formed vapours is subsequently epoxydized, for example by using a peracid. To this end, peracetic acid is preferred.

The last step of the above described process consists in heating up the obtained epoxyde. Of course, this operation can be carried out at temperature varying within a wide range of values, for instance at temperature of between about 400 and 550° C. As usual in analogous cases, at lower temperatures the course of the reaction time is rather slow whereas at temperatures higher than the above given upper limit, it is difficult to better control the formation of undesirable by-products.

The obtained pyrolysate is constituted eminently by 1(7)-p-menthen-9-al accompanied by the two compounds of formula

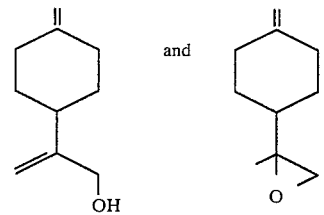

The presence of these compounds does not seem to exert any adverse effect on the main fragrance character of 1(7)-p-menthen-9-al. Consequently, a purification of the mixture directly obtained by the invention process is not compulsory. Should one desire nevertheless to purify further the obtained compound, then a simple fractional distillation will suffice.

The process of the invention is illustrated by the following reaction scheme:

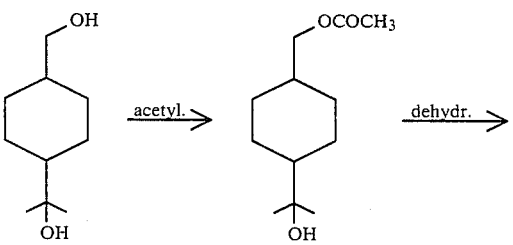

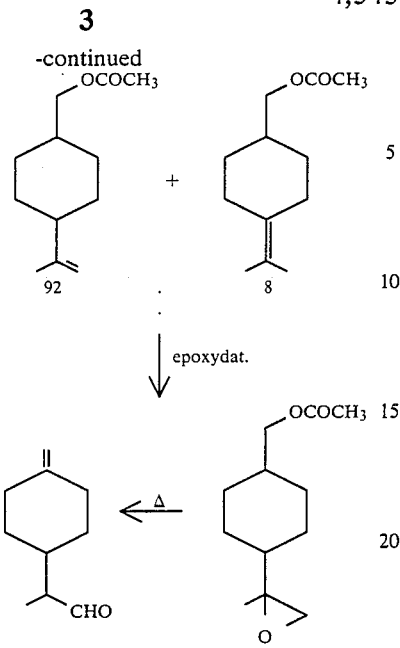

7,8-Dihydroxy-p-menthane, used as starting material in the process of the invention can be prepared from B-pinene according to a process which can be illustrated as follows:

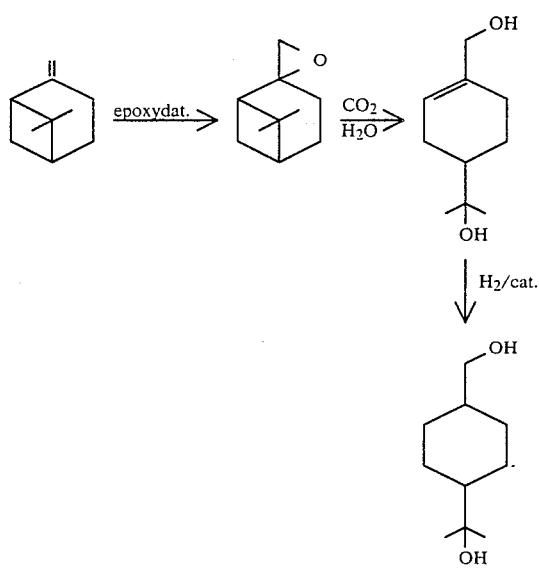

The invention is better illustrated by the following examples wherein the temperatures are indicated in degrees centigrade and the abbreviations have the meaning usual in the art.

Example 1

Preparation of 1(7)-p-menthen-9-al a. 7-Acetoxy-8-hydroxy-p-menthane

A mixture of 258 g (1.5 M) of 7,8-dihydroxy-p-menthane, 2700 ml of acetic anhydride and 810 ml of pyridine was kept under stirring for 45 minutes, then it was poured onto ice (1 kg) and water (1000 ml). After its extraction with three fractions of 700 ml each of ether, the combined organic phases were washed with a 10% aqueous solution of NaOH (3×500 ml), water (2×500 ml) and a saturated aqueous solution of NaCl (500 ml). The solvent was evaporated and the residue (284 g) was distilled to give a colorless oil (276 g) having b.p. 108–110°/0.133 Pa (yield 86%).

MS:$M^+$ =214;m e:43,59,81,96.

b. 7-Acetoxy-8-p-menthane

A solution of 60 g (0.28 M) of the hydroxy-acetate obtained sub letter a. above in 60 ml of hexane was poured on the top of a pyrex column, of 30 cm length and 2 cm internal diameter, filled on ⅔ of its length with a mixture of γ-alumina (2.5 g) and quartz (50 g). The column was heated at 250° while a constant flow of nitrogen was passed through at a rate of 100 ml/min.

The products formed were condensed by making use of two communicating traps cooled at −70°. The condensate was diluted with 140 ml of hexane then, upon separation, the organic phases were dried over $MgSO_4$. Subsequent evaporation of the solvent gave 51.6 g of a 92:8 mixture of 7-acetoxy-8-p-menthene and 7-acetoxy-4(8)-p-menthene (yield 82%). MS:$M^+$ =196;m/e: 43,93,107,79.

c. 7-Acetoxy-8,9-epoxy-p-menthane

A mixture of 40% peracetic acid (34 g) and sodium acetate (7 g) was added dropwise (about 2 h) under stirring to a mixture of 25 g of the product obtained under letter b. above, 40 g of sodium carbonate and 300 ml of methylene chloride. The reaction mixture was then kept under stirring for 5 h, then it was filtered. The clear filtrate was successively washed with water, with a 10% solution of $Na_2SO_3$ and then with water again. After evaporation of the volatiles under reduced pressure, 23.2 g of the desired raw material was obtained (purity of 88%) in the form of a 75/25 cis/trans isomeric mixture (yield 80%). This mixture can be used directly for the following reaction step.

MS:$M^+$ =212; m/e:43,95,41,79.

d. 1(7)-p-Menthen-9-al

A solution of 5 g of the product obtained according to letter c. above in 100 ml of hexane was introduced, by means of piston pump, at a rate of 0.5 ml/min, at the top of an empty quartz column (length: 400 cm; int. diameter: 0.8 cm) heated at 500° and kept under a constant flow of nitrogen of 13 ml/min. The vapors formed were cooled at −70° and thus condensed in two communicating traps, the first of which contained 1 g of sodium bicarbonate. The pyrolysate was then washed successively with a 5% aqueous solution of sodium bicarbonate, 5% HCl, water and a saturated NaCl aqueous solution. After drying over $Na_2SO_4$ the separated organic phase was concentrated.

Four different runs were carried out as indicated above on identical quantities of starting 7-acetoxy-8,9-epoxy-p-menthane. 15.5 g of a crude mixture containing 40% of the desired menthenal were thus obtained. On distillation on a Vigreux column, it was possible to enrich the content of menthenal in the mixture to 60%. This content can be further enriched to 95%, or even more, by means of fractional distillation using a Fischer type column.

An analytical sample could be prepared in such a way. The analytical characters of the obtained product were as follows:

NMR($CDCl_3$):9.1;8.96;7.95-8.35;7.76;5.41 ∂ppm;

MS:$M^+$ =152;m/e:79,84,94,41;

IR:2940,1720,1655,1455,900 cm$^{-1}$.

7,8-Dihydroxy-p-menthane, used as starting material in the above described process, was prepared according to the method prior illustrated starting from β-pinene. The first step consists in the epoxydation of this latter compound according to J. K. Crandall and Luan-Ho C. Lin, Org. Chem. 33,2375 (1968). The obtained epoxyde was then treated with water saturated with $CO_2$ under vigorous stirring. By extraction with ether and distillation of the volatiles, 7,8-dihydroxy-p-menthane was obtained in a 90% yield, b.p. 70°–115°/1.33 Pa. By catalytic hydrogenation of the said compound the desired 7,8-dihydroxy-p-menthane was obtained with a good yield.

EXAMPLE 2

A base perfume composition of hyacinth type was prepared by mixing the following ingredients (parts by weight):

| | |
|---|---|
| Cinnamic alcohol | 2150 |
| Phenethylol | 2265 |
| Benzyl acetate | 1200 |
| Methyl jasmonate | 650 |
| Methyl isoeugenol | 650 |
| Hexylcinnamaldehyde | 1250 |
| Terpineol | 250 |
| Synth. hydroxycitronellal | 350 |
| Galbanum oil 10%* | 325 |
| Indol 10%* | 300 |
| Pipol 10%* | 200 |
| Pipol acetate 10%* | 100 |
| Phenylacetaldehyde 10%* | 250 |
| | 9940 |

*in diethyl phthalate

By adding to the above composition 60 g of 1(7)-p-menthen-9-al, a novel composition resulted whose fragrance is naturally fresh and lifting. The addition of menthenal enhances the green top notes and the flowery character of the composition.

EXAMPLE 3

A base perfume composition of fougère type was prepared by mixing the following components (parts by weight):

| | |
|---|---|
| Amyl salicylate | 1600 |
| Synth. bergamot oil | 3700 |
| Cumarin | 500 |
| Geranium oil | 400 |
| Lavender oil | 1000 |
| Oak-moss 10%* | 2750 |
| | 9950 |

*in dipropylene glycol

By adding to the above composition 50 g of 1(7)-p-menthen-9-al, a novel composition was obtained with a warm, aromatic and spicy character reminiscent of cumin and caraway.

What we claim is:

1. 1(7)-p-Menthen-9-al of formula

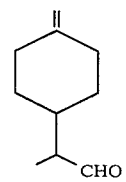

(I)

2. A process for the preparation of 1(7)-p-menthen-9-al according to claim 1, which comprises:
   (a) treating 7,8-dihydroxy-p-menthane with acetic anhydride to give 7-acetoxy-8-hydroxy-p-menthane;
   (b) dehydrating the obtained compound with alumina to yield 7-acetoxy-8-p-menthane;
   (c) epoxydizing this latter compound with a peracid to give 7-acetoxy-8,9-epoxy-p-menthane, and
   (d) subjecting the said epoxyde to a thermal treatment at a temperature between 450° and 550° C. to give a pyrolysate essentially consisting of the desired 1(7)-p-menthen-9-al.

* * * * *